United States Patent [19]

Trapasso et al.

[11] Patent Number: 5,606,103

[45] Date of Patent: *Feb. 25, 1997

[54] ORGANOTIN CATALYZED TRANSESTERIFICATION

[75] Inventors: Louis E. Trapasso, West Long Branch; Philip L. Meisel, Greenbrook; Lee B. Meisel, Holmdel, all of N.J.; Willy K. Chwang, Germantown, Tenn.

[73] Assignee: CPS Chemical Company, Inc., Old Bridge, N.J.

[*] Notice: The term of this patent shall not extend beyond the expiration date of Pat. No. 5,498,751.

[21] Appl. No.: 580,181

[22] Filed: Dec. 28, 1995

Related U.S. Application Data

[63] Continuation-in-part of Ser. No. 473,188, Jun. 7, 1995, Pat. No. 5,554,785, which is a continuation-in-part of Ser. No. 116,448, Sep. 3, 1993, Pat. No. 5,498,751.

[51] Int. Cl.$^6$ .................................................. C07C 67/02
[52] U.S. Cl. ................................................................ 560/217
[58] Field of Search ................................................ 560/217

[56] References Cited

U.S. PATENT DOCUMENTS

| | | |
|---|---|---|
| 3,328,439 | 6/1967 | Hamilton . |
| 3,642,877 | 2/1972 | Madhusudan . |
| 3,663,569 | 5/1972 | Lew . |
| 3,686,768 | 8/1972 | Jobert et al. . |
| 3,714,234 | 1/1973 | White . |
| 4,112,235 | 9/1978 | Schmerling . |
| 4,229,362 | 10/1980 | Norman . |
| 4,281,175 | 7/1981 | Kametani et al. . |
| 4,301,297 | 11/1981 | Kametani et al. . |
| 4,473,702 | 9/1984 | Seguchi . |
| 4,547,585 | 10/1985 | Yamanaka et al. . |
| 4,667,044 | 5/1987 | Nees et al. . |
| 4,677,225 | 6/1987 | Nizuma et al. . |
| 4,745,213 | 5/1988 | Schlosser et al. . |
| 4,845,266 | 7/1989 | Marx et al. . |
| 4,904,814 | 2/1990 | Frei et al. . |
| 4,983,761 | 1/1991 | Brewer et al. . |
| 5,286,896 | 2/1994 | Korte et al. . |
| 5,338,882 | 8/1994 | Korte et al. . |
| 5,498,751 | 3/1996 | Trapasso et al. ................. 500/217 |

FOREIGN PATENT DOCUMENTS

| | | |
|---|---|---|
| 394571 | 5/1992 | Austria . |
| 2140304 | 7/1995 | Canada . |
| 85102522 | 7/1986 | China . |
| 262589 | 7/1989 | Czechoslovakia . |
| 4317428 | 6/1994 | Germany . |
| 54-41814 | 4/1979 | Japan . |
| 54-70215 | 6/1979 | Japan . |
| 58-170730 | 10/1983 | Japan . |
| 8637337 | 2/1986 | Japan . |
| 63-115850 | 5/1988 | Japan . |
| 01265058 | 10/1989 | Japan . |
| 02067264 | 3/1990 | Japan . |
| 3-041051 | 2/1991 | Japan . |
| 04095054 | 3/1992 | Japan . |

OTHER PUBLICATIONS

Yu et al., *Huaxue Xuebao*, 48(3), 287–94 (1990).
Otera et al., *Tetrahedron Lett.*, 27(21), 2383–6 (1986).
Otera et al., *J. Org. Chem.*, 54, 4013–14 (1989).
Otera et al., *J. Org. Chem.*, 56(18), 5307–11 (1991).
Aldrich, 33, 568–1, 1992.
CA 91:192843/AN (1976).

*Primary Examiner*—Samuel Barts
*Attorney, Agent, or Firm*—Lerner, David, Littenberg, Krumholz & Mentlik

[57] ABSTRACT

Methyl or ethyl esters of mono- and polycarboxylic acids are transesterified with alcohols and polyols by reaction in the presence of a catalytically effective amount of organotin catalyst, so that an alcohol or polyol carboxylic acid ester is formed, which is then washed with aqueous alkali having a pH bigger than about 13.2 so as to remove essentially all of the organotin catalyst, thereby permitting the recovery of the alcohol or polyol carboxylic acid ester essentially free of the organotin catalyst.

19 Claims, No Drawings

ORGANOTIN CATALYZED TRANSESTERIFICATION

CROSS-REFERENCE TO RELATED APPLICATION

This application is a Continuation-In-Part of U.S. patent application Ser. No. 08/473,188 filed Jun. 7, 1995, now U.S. Pat. No. 5,554,785 which application in turn is a Continuation-In-Part of U.S. patent application Ser. No. 08/116,448, filed Sep. 3, 1993, now U.S. Pat. No. 5,498,751. The disclosures of both applications are incorporated herein by reference.

BACKGROUND OF THE INVENTION

The present invention relates to methods for recovering higher esters of carboxylic acids substantially free of the organotin catalyst which has catalyzed a transesterification reaction between lower alkyl esters of the carboxylic acid and alcohols or polyols.

Esters of unsaturated carboxylic acids and of aromatic polycarboxylic acids are of increasing commercial importance as polymerizable monomers. Materials of this nature are used to form both homopolymers and copolymers; which have commercial uses in many applications. Such applications include coatings for paper products, waste water treatment systems, optical lens coatings, floor polishes, anaerobic adhesives, pour point depressants, paper coatings, UV and EB coatings and adhesives, textile finishes, pressure sensitive adhesives, viscosity index improvers, potting compounds and sealants, photopolymers for electronics and printing plates, rubber and plastics modifiers, UV curable inks and overprint varnishes, dental and medical resins, reactive diluents for radiation curable oligomers, crosslinkers for rubber vulcanization, moisture barrier films, ion exchange resins, PVC plastisols, encapsulation and impregnation of small diameter spheres, leather finishes, binder resins for sand castings, UV curable resins for imaging systems, silane intermediates, and the like; such applications being well known to those skilled in the art.

One group of monomers of particular interest are the polyfunctional monomers; that is to say, esters of unsaturated carboxylic acids with polyfunctional alcohols. As is also well known to those skilled in the art, materials of this nature can be used as crosslinking agents to form rigid coatings which are insoluble in normally used solvents. Of particular interest are the esters of acrylic acid (2-propenoic acid) and methacrylic acid (2-methyl-2-propenoic acid). These esters, both monofunctional and polyfunctional, have long been used as components of homopolymers and/or copolymers for the applications described above.

Another group of monomers of particular interest are the unsaturated esters of aromatic polycarboxylic acids. The polymerization products of such monomers possess excellent dielectric properties, dimensional stability, heat resistance, weatherproof-ness, solvent resistance and mechanical properties. Preferred polymer products also possess optimum optical properties, including transparency, refractive index and surface hardness. Such polymers are desirable for use as optical materials.

In the past, as in current industrial practice, the above monomers have been made by direct esterification, i.e., the acid catalyzed reaction of an unsaturated carboxylic acid with a mono- or polyhydric alcohol. The major exception to this is the preparation of unsaturated esters containing a basic functional group, such as an amine group. In these cases, the products have traditionally been made by a transesterification procedure, using catalysts such as sodium methylate, lead oxide, tetraisopropyl titanate, and the like. (See, e.g., U.S. Pat. No. 3,642,877.) In the commercial preparation of compounds of this type, the final reaction mixture is subjected to fractional distillation under reduced pressure, in order to obtain the desired monomer in a state of high purity, free of the metallic catalyst and/or polymerization inhibitor, which must be present during the preparation of these compounds.

By contrast, the products of the acid-catalyzed direct esterification are purified by base-washing procedures, which will remove acid catalyst and excess unreacted carboxylic acid as well as polymerization inhibitors. Although, in principle, it would be possible also to purify such reaction products by fractional distillation under reduced pressure, in industrial practice this procedure is only used with materials of relatively high volatility. This is because many of these products, particularly the esters of long-chain aliphatic alcohols as well as the esters of polyhydric alcohols, have relatively high boiling points, even when high vacuum is employed, making them very difficult to distill. As is well known in the art, monomers of this nature will tend to polymerize at temperatures in excess of about 115°–120°, even when inhibited with various polymerization inhibitors. Consequently, in industrial practice, it is preferred to isolate the reaction products as "bottoms" products, which are not distilled.

The acid-catalyzed direct esterification described above suffers from various disadvantages, particularly the occurrence of several side reactions. In particular, such processes may cause the formation of color bodies which may be difficult, if not impossible, to remove from the finished product. Such color bodies may render the product unsuitable for many industrial applications, in particular in areas such as paper treatment chemicals, industrial coatings and the like. Also, the acid-catalyzed side reactions will lead to the production of by-products. Such by-products, although not necessarily deleterious in themselves, act as unreactive diluents for the final product and thus reduce its efficacy. Other disadvantages include the need to use an excess of the carboxylic acid to complete the reaction. This excess carboxylic acid cannot generally be recovered and recycled; and therefore represents an extra raw material cost as well as an increased waste disposal cost.

It is, of course, possible to prepare many of these products by transesterification, but many of the same disadvantages will remain. In particular, many potential transesterification catalysts such as aluminum isopropoxide, sodium methoxide, tetraisopropyl titanate and lead oxide, also catalyze the same side reactions described above. A further disadvantage is that many of these catalysts are difficult, if not impossible, to remove from the finished product, especially on an industrial scale.

A metal-containing catalyst system made from dialkyltin dichloride has been reported. Otera et al., *J. Org. Chem.*, 54, 4013–14 (1989) discloses that dialkyltin dichlorides form distannoxanes that are stable, rigid, ladder structures (with four tin atoms), which function as a template that exercises steric control during transesterification. These materials have been described as "reverse micelies" whose structure has to remain intact in order to be catalytic. This reference, however, contains no disclosure regarding how to isolate the pure product ester, a step which is essential to commercial manufacture.

Otera et al., *J. Org. Chem.*, 56(18), 5307–11 (1991) disclose these compounds to be effective catalysts in the transesterification of monohydric alcohols. This is confirmed by Otera et al., *Tetrahedron Lett.*, 27(21), 2383–6 (1986), which also discloses the transesterification of diols other than 1,2- and 1,3-diols.

U.S. Pat. No. 4,473,702 discloses the synthesis of a diallyl ester of an aromatic dicarboxylic acid by transesterification with allyl alcohol. The reaction is catalyzed by a dialkyltin dichloride, dialkyltin oxide or mixtures thereof in combination with a second catalyst such as metallic magnesium, zinc, tin, lead, aluminum, nickel or zirconium, or oxides thereof. The disclosure of this patent is limited to reactions employing monohydric alcohols and the resulting ester is separated by conventional distillation and recrystallization methods, with no indication that the ester is obtained in a pure form free of the metal catalyst.

DE 4,317,428 discloses transesterification reactions catalyzed by a mixture of a dialkyl tin dichloride and a dialkyl tin dicarboxylate, in which the alkyl groups contain from 1 to 12 carbon atoms. Alternatively, a dialkyl tin chloride monocarboxylate or an alkyl tin chloride dicarboxylate in which the alkyl groups contain from 1 to 12 carbon atoms, may be used as the transesterification catalyst. The examples depict the use of dibutyl tin dichloride, dibutyl tin dicarboxylate, and blends thereof as transesterification catalysts. Such catalyst systems do not allow for recovery of the nondistillable esters in pure form free of the tin catalyst.

None of the foregoing publications disclose a transesterification catalyst or method that will allow for the isolation of pure nondistillable product esters. There remains a need for a catalyst system effective in the transesterification of alcohols and polyols with mono- and polycarboxylic acids that permits the isolation of the pure nondistillable ester product free of the metal catalyst.

SUMMARY OF THE INVENTION

Organotin catalysts can be used in an unexpectedly different manner than described in the above-cited references to provide heretofore unattainable nondistillable transesterification products in high yield and of excellent purity. The process of the present invention provides a simplified method of catalyst removal. The products prepared in accordance with the methods of the present invention are substantially colorless and free of by-products and metallic catalysts.

The present invention incorporates the discovery that residual organotin catalysts can be removed from reaction mixtures by a simple aqueous caustic wash without distillation. An acid wash may enhance the removal of the organotin catalyst residues from the final product. The relative solubility of the organotin catalyst residue in dilute aqueous caustic is determined by the size of the hydrophobic alkyl group(s) attached to the tin atom. In particular, the total number of carbon atoms in alkyl group(s) directly attached to each tin atom should not exceed four. Therefore, in accordance with one embodiment of the present invention, there is provided a method for transesterifying methyl or ethyl esters of carboxylic acids with alcohols or polyols, including the steps of:

(A) providing a reaction mixture including:

(1) an alcohol or polyol selected from the group consisting of aralkyl, aliphatic and cycloaliphatic alcohols and polyols; and (2) a methyl or ethyl ester of a carboxylic acid selected from mono- and polycarboxylic acids;

provided that the reaction mixture does not include a mixture of a polyol with a polycarboxylic acid;

(B) reacting the mixture at a temperature at which the alcohol or polyol and the carboxylic acid are liquid, and in the presence of a catalytically effective amount of an organotin catalyst having the structure:

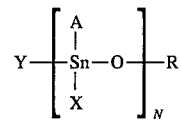

wherein, for each Sn, A is independently selected from alkyl groups containing from one to four carbon atoms, and X is independently selected from alkyl, chlorine, bromine, hydroxyl, 1 to 18 carbon atom alkoxy and 1 to 18 carbon atom acyloxy groups, provided that when X is alkyl, the total number of carbon atoms in A and X for each Sn is no more than 4, and when X is not alkyl, the total number of carbon atoms in A for each Sn is no more than 4;

Y is selected from chlorine, bromine, hydroxyl, 1 to 18 carbon atom alkoxy and 1 to 18 carbon atom acyloxy groups, R is selected from hydrogen, 1 to 18 carbon atom alkyl and 1 to 18 carbon atom acyl groups or Y, X and -O-R together form a stannanoic acid group or an anhydride thereof; and N is an integer from 1 to 10;

so that an alcohol or a polyol ester of the carboxylic acid and methanol or ethanol are formed;

(C) washing the reaction mixture with aqueous alkali having a pH greater than about 13.2, so as to remove essentially all of the organotin catalysts; and (D) recovering the alcohol or polyol carboxylic acid ester essentially free of the organotin catalyst.

The present invention also incorporates the discovery that residual organotin catalysts can be recovered from reaction mixtures using a strong aqueous acid wash. An additional caustic wash is still necessary to remove phenolic inhibitors. This may nevertheless be advantageous because sequential acid and alkali washing steps may serve to further reduce the residual tin in the final product. Therefore, methods in accordance with the present invention may optionally further include the step of washing the reaction mixture with aqueous acid at a pH less than about 1.5 before the step of washing the reaction mixture with aqueous alkali.

The methods of the present invention are particularly well suited for the transesterification of acrylate and methacrylate esters. Another feature of this method is that the organotin catalyst can be prepared in situ. Methods in accordance with this aspect of this embodiment of the present invention further include a catalytically effective amount of a monoalkyltin trichloride or a dialkyltin dichloride having less than or equal to four carbon atoms directly attached to each tin atom in the reaction mixture. The reaction step then further includes the step of heating the reaction mixture so that solvolysis of one or more tin-chlorine bonds occurs to generate a catalytically effective amount of the organotin catalyst.

Reaction mixtures in accordance with this aspect of this embodiment of the present invention preferably further include an HCl acceptor compound. Such compounds promote the in situ formation of the organotin catalyst. Reaction mixtures in accordance with this aspect of this embodiment of the present invention may also preferably further include a salt of a carboxylic acid containing up to 18 carbon atoms. Such compounds promote the in situ formation of organotin catalysts with acyloxy groups containing up to 18 carbon atoms. For example, reaction of a dialkyltin dichloride with sodium acetate leads to formation of a dialkyltin diacetate which is immediately effective as a catalyst.

The combination of techniques described above permits the preparation of higher esters of carboxylic acids as "bottoms" products on an industrial scale. Other features of the present invention will be pointed out in the following description and claims, which disclose, by the way of example, the principles of the invention and the best modes which have been presently contemplated for carrying them out.

DETAILED DESCRIPTION OF THE PREFERRED EMBODIMENT

The transesterification reactions of the present invention can be described in terms of the following equation:

$$R(OH)_n + nR_1OCOA \leftrightarrows R(OCOA)_n + nR_1OH \qquad (I)$$

In this equation, $R(OH)_n$ represents the alcohol or polyol whose ester is to be prepared, $R_1OH$ is the monohydric alcohol whose ester is used in the transesterification reaction; and A represents the acid (e.g. if $A=-CH=CH_2$, then an acrylate is the product) from which the esters are derived. The variable n is an integer whose value can be one or greater, preferably from one to four.

The transesterification process of the present invention is operative for essentially any mono- or polycarboxylic acid ester derivative. In the above-depicted reaction scheme, A can represent an aromatic, aliphatic or cycloaliphatic mono- or polycarboxylic acid residue.

The aliphatic and cycloaliphatic carboxylic acid residues may be derived from saturated, monounsaturated and polyunsaturated carboxylic acids. These acids may be straight-chained or branched and may be substituted. The aliphatic and cycloaliphatic carboxylic acid residues represented by A preferably contain between about 2 and about 30 carbon atoms, and more preferably contain between about 3 and about 20 carbon atoms.

While the transesterification method of the present invention is functional with respect to essentially any carboxylic acid ester starting material, esters of aromatic and unsaturated aliphatic and cycloaliphatic carboxylic acids are preferred because of the utility of their transesterification product as monomers. The unsaturated bonds of the aliphatic and cycloaliphatic carboxylic acid esters serve as polymerization sites. The aromatic carboxylic acid esters, on the other hand, are preferably transesterified with an unsaturated alcohol, the double bonds of which serve as polymerization sites. While the method of the present invention can be used to synthesize higher esters of saturated aliphatic and cycloaliphatic carboxylic acids and saturated esters of aromatic carboxylic acids, these materials, unlike the preferred compounds, can be produced by the more vigorous reaction conditions of direct esterification.

$R_1$ in the above-depicted reaction scheme represents the alcohol portion of the carboxylic acid ester starting material. The transesterification process of the present invention results in the formation of a monohydric alcohol containing this group. While $R_1$ can represent essentially any lower alkyl group for the transesterification process of the present invention to proceed, for all practical purposes, $R_1$ is methyl or ethyl.

Particularly preferred mono- and polycarboxylic acid ester starting materials include methyl and ethyl acrylate, methyl and ethyl methacrylate, methyl and ethyl benzoate, methyl and ethyl phthalate, methyl and ethyl trimellitate, methyl and ethyl terephthalate, methyl and ethyl isophthalate, methyl and ethyl naphthalene di- and tricarboxylates, methyl and ethyl benzene tricarboxylates, and the like. The transesterification process of the present invention will produce higher esters of these carboxylic acids.

R of the above-depicted reaction scheme represents the alcohol portion of the ester to be formed in the transesterification reaction of the present invention, with $R(OH)_n$ representing the monohydric or polyhydric alcohol starting material whose ester is to be prepared. For purposes of the present invention, R will be defined as the residue of the alcohol or polyol starting material whose ester is to be prepared by the disclosed transesterification process.

In the processes of the present invention, R represents the residue of an aralkyl, aliphatic or cycloaliphatic alcohol or polyol. The alkyl groups of the aralkyl alcohols or polyols are hydroxyl-substituted. The aralkyl alcohols and polyols from which the residue R is derived may contain a single or multiple aromatic ring or a fused ring system. Any aromatic ring may be substituted or unsubstituted. Aralkyl alcohol and polyol residues in accordance with the present invention preferably contain between about 7 and about 20 carbon atoms, and more preferably contain between about 8 and about 12 carbon atoms.

The aliphatic or cycloaliphatic alcohols and polyols from which the residue R is derived may be saturated, monounsaturated or polyunsaturated. The alcohol and polyol residues may be straight-chained or branched, and substituted or unsubstituted. The alcohol and polyol residues represented by R preferably contain between about 2 and about 40 carbon atoms, and even more preferably contain between about 3 and about 26 carbon atoms.

Particularly preferred alcohols and polyols for use in the transesterification process of the present invention include n- or iso- 8 to 22 carbon atom alkanols, furfuryl alcohol, tetrahydrofurfuryl alcohol, benzyl alcohol, 2-phenoxy-ethanol, cyclohexanol, allyl alcohol, methallyl alcohol, crotyl alcohol, ethylene glycol, triethylene glycol, 1,3-butanediol, trimethylolpropane, pentaerythritol, dipentaerythritol, 2,2-dimethyl-1,3-propanediol, glycerine, and the like. When reacted with methyl or ethyl acrylate or methacrylate, the transesterification process of the present invention produces higher esters of acrylic or methacrylic acid.

The transesterification process of the present invention is operative for the combination of essentially any aralkyl, aliphatic or cycloaliphatic polyol starting materials with essentially any aromatic, aliphatic or cycloaliphatic monocarboxylic acid, or with any aralkyl, aliphatic or cycloaliphatic alcohol with essentially any aromatic, aliphatic or cycloaliphatic mono- or polycarboxylic acid. The combination of polyols with polycarboxylic acids is undesirable because the reactants crosslink to form non-useful reaction products.

As noted above, the process of the present invention is particularly well suited for unsaturated starting materials. This is because unsaturated alcohols, polyols and carboxylic acids are sensitive to the more vigorous direct esterification conditions. Commercially useful monomers are typically obtained by reacting an aralkyl or saturated aliphatic or cycloaliphatic alcohol with an unsaturated aliphatic or cycloaliphatic mono- or polycarboxylic acid ester, or by reacting an unsaturated alcohol with an aromatic or saturated aliphatic or cycloaliphatic mono- or polycarboxylic acid ester. Commercially useful monomers are also obtained by reacting an aralkyl or saturated aliphatic or cycloaliphatic polyol with an unsaturated aliphatic or cycloaliphatic monocarboxylic acid ester.

Unexpectedly unique results are obtained for the transesterification of essentially any alcohol with essentially any mono- or polycarboxylic acid ester, or for the transesterification of essentially any polyol with essentially any monocarboxylic acid ester, using the organotin catalyst systems of the present invention. When the organotin catalyst system is employed, the transesterification product obtained after simple alkaline washing is essentially free of the organotin catalyst.

The relative solubility of the organotin catalyst residues in dilute aqueous caustic is determined by the size of the hydrophobic alkyl group(s) attached to tin. For example, a catalyst derived from dimethyltin dichloride is soluble in dilute aqueous caustic, while catalysts derived from dibutyltin dichloride, however, are insoluble in dilute aqueous caustic. Similarly, catalysts derived from butyltin trichloride are soluble in dilute aqueous caustic. Catalysts derived from octyltin trichloride behave like a surfactant and are not soluble in excess dilute caustic. Therefore, the organotin catalysts must have either one or two alkyl-tin bonds per tin atom, wherein the one or two alkyl groups contain no more than a total of four carbon atoms for ease of removal with caustic.

Organotin catalysts with greater than four carbon atoms in alkyl groups attached to tin can be removed from reaction mixtures but an aqueous acid wash may be required prior to a dilute caustic wash. For example, the use of n-octyltin trichloride (and sodium methoxide) for preparation of isodecyl methacrylate gave a clean split with 37% hydrochloric acid that permitted easy separation of the organic phase from the aqueous acid phase. A subsequent 20% caustic wash caused an insoluble precipitate to collect at the interface which was discarded as part of the aqueous phase. After neutralization of the wet organic phase by washing the wet organic phase with a sodium chloride brine solution and removal of solvent, a 95% yield of isodecyl methacrylate was obtained. The final product contained 1940 ppm Sn by atomic absorption spectroscopy which represented 85% catalyst removal.

The selection and preparation of organotin compounds useful for transesterification of alcohols by methyl or ethyl esters have previously been described (U.S. Ser. No. 08/116, 448). Particularly useful are those organotin compounds derived from monoalkyltin trihalides or dialkyltin dihalides by solvolysis of tin-halide bonds. For example, the hydrolysis of dibutyl tin dichloride with aqueous caustic gives dibutyltin oxide which is an excellent transesterification catalyst. Stannic chloride ($SnCl_4$), stannous chloride ($SnCl_2$) and their solvolysis products are poor transesterification catalysts. The tetraalkyl tins do not undergo solvolysis readily or possess catalytic activity. Furthermore, the organotin compounds derived from the trialkyl tin monohalides are poor transesterification catalysts.

To be useful as a transesterification catalyst, particularly for the manufacture of acrylate or methacrylate monomers of this invention, the tin halide compound from which the catalyst is derived must have either one or two alkyl-tin bonds, and, as noted above, with the one or two alkyl groups containing no more than a total of four carbon atoms. Catalysts derived from the monoalkyl tin trihalides can be substituted for dialkyltin dihalides in most cases for the transesterification of simple primary and secondary alcohols. In each case an active form of the catalyst is obtained by solvolysis of at least one tin-chloride bond. For immediate catalysis without an induction period, the solvolysis can be enhanced by the addition of a base like sodium methoxide or sodium acetate to the reaction mixture along with the organotin halide so that the active form of the catalyst is developed rapidly in situ. Furthermore, dialkyltin dicarboxylates are less efficient catalysts by themselves for transesterification of 1,3- and 1,2-glycols. However, an equimolar combination of a dialkyltin dihalide and each of the above (oxide, dialkoxide or dicarboxylate) results in a rapid reaction. As shown in example 1 below, neopentyl glycol (a 1,3 glycol) is efficiently transesterified using a combination of dimethyltin dichloride with tetramethyldiacetoxy-distannoxane.

Up to and including all three of the chlorides per mole of an alkyltin trichloride can be replaced (e.g., with alkoxide groups) without losing catalytic activity for the transesterification of simple monofunctional primary and secondary alcohols. When all three chlorides atoms are replaced, the resulting alkyl stannanoic acid, as well as its ester and/or anhydride, are all effective transesterification catalysts. A loss in catalytic activity is observed if excess base is present such that the salt of the alkyl stannanoic acid (e.g., amine salt or alkali metal salt) is formed. Ordinarily, the replacement of the last (3rd) chloride by alkaline hydrolysis is not readily achieved and this chloride may not be removed under transesterification reaction conditions. This is not necessary for catalysis as transesterification begins as soon as one chloride is replaced. However, catalytic activity remains when an alkyl $SnCl_3$ is used with three moles of sodium methoxide per mole of alkyl $SnCl_3$.

For example, monobutyltin dihydroxide monochloride ($BuSn(OH)_2Cl$) is a stable substance formed by the hydrolysis of $BuSnCl_3$. It can be purchased as a crystalline white solid. This material is an excellent transesterification catalyst for primary and secondary alcohols. Glycols can be transesterified as long as the OH groups are located more than three carbon atoms apart. Monobutyltin dihydroxide monochloride can also be heated under vacuum and converted upon the loss of water into an oligomeric polystannoxane. These oligomers are just as effective in catalyzing transesterification as the starting $BuSn(OH)_2Cl$. Equivalent properties are also obtained from monoalkyltin catalysts with lower alkyl groups.

Solvolysis products of alkyl $SnCl_3$ containing two or more chlorides per mole of alkyl $SnCl_3$ are catalysts for the transesterification of 1,2 and 1,3 glycols, but that catalytic activity diminishes after replacement of two or more chlorides per mole of alkyl $SnCl_3$. This complication does not exist if the hydroxyl groups are more than three carbon atoms apart. Thus, monoalkyltin dihydroxide monochloride, alkylstannanoic acid or monoalkyltin oxide (alkylstannanoic acid anhydride) are not as effective for the transesterification of 1,2- and 1,3-glycols.

In general, the active forms of these organotin catalysts which can be removed from acrylate and methacrylate transesterification reaction mixtures by washing with dilute aqueous caustic are represented as follows:

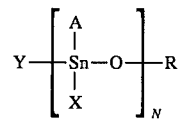

wherein, for each Sn, A is independently selected from alkyl groups containing from one to four carbon atoms and X is independently selected from alkyl, chlorine, bromine, hydroxyl, 1 to 18 carbon atom alkoxy and 1 to 18 carbon atom acyloxy groups, provided that, when X is alkyl, the total number of carbon atoms in A and X for each Sn is no more than four, and when X is not alkyl, the total number of carbon atoms in A for each Sn is no more than four.

Y is selected from chlorine, bromine, hydroxyl, 1 to 18 carbon atom alkoxy and 1 to 18 carbon atom acyloxy groups; R is selected from hydrogen, 1 to 18 carbon atom alkyl and 1 to 18 carbon atom acyl groups or Y, X and -O-R together form a stannanoic acid group or an anhydride thereof; and N is an integer from 1 to 10. When N is greater than one, A and X may vary from tin atom to tin atom.

While the alkyl groups for A and X for each Sn must contain no more than a total of four carbon atoms for each Sn, the alkoxy and acyloxy groups of X and Y, and the alkyl and acyl groups of R, can contain up to 18 carbon atoms, because such groups are readily hydrolyzed from the tin atom and removed from the reaction mixture by the dilute aqueous caustic wash.

The above-depicted reaction scheme is carried out by first charging a reactor with the alcohol or polyol, followed by the methyl or ethyl ester of the mono- or polycarboxylic acid. The molar ratio of the methyl or ethyl ester of the carboxylic acid to the alcohol or polyol can be varied over a wide range and can be readily determined by one of ordinary skill in the art without undue experimentation.

A reaction temperature is selected at which the alcohol or polyol and the methyl or ethyl carboxylic acid ester are liquid. This will vary considerably because of the wide variety of carboxylic acid esters, alcohols and polyols that can be utilized with the inventive process. However, the selection of a reaction temperature at which the reactants are liquid is a matter that can be readily determined by one of ordinary skill in the art without undue experimentation.

The reaction is carried out in the presence of the organotin catalyst. Typically, the catalyst is present at a level between about 0.01 and about 2.00 percent by weight, and more preferably at a level between about 0.05 and about 1.00 percent by weight.

Another feature of the method of the present invention is that the organotin catalyst can be prepared in situ from monoalkyltin trichlorides or dialkyltin dichlorides having no more than four carbon atoms. The catalyst is formed in situ by including dialkyltin dichloride in the reaction mixture, which converts to the organotin catalyst by solvolysis under reaction conditions, although the transesterification reaction rate is initially slower at first until an effective quantity of the monoalkytin trichloride or dialkyltin dichloride has been converted (solvolyzed).

The in Situ formation of the organotin catalyst can be promoted by the addition of an HCl-acceptor or alkali base to the reaction mixture, such as an alkali metal hydroxide or alkoxide, an alkaline earth metal hydroxide or oxide, an alkali or alkaline earth metal carbonate or bicarbonate, an alkali or alkaline earth carboxylate, tribasic alkali phosphates, organic bases such as tertiary amines, and the like. The alkoxy groups of X, Y and -O-R are obtained by using alkali metal alkoxides containing from 1 to 22 carbon atoms. Preferred alkali metals include lithium, sodium and potassium. Preferred alkoxides include methoxides such as sodium methylate, sodium ethoxides and sodium alkoxides of the alcohol to be transesterified. The preferred alkaline earth metal is magnesium and calcium, and the preferred tertiary amine is triethylamine. The molar ratio of the HCl-acceptor to monoalkyltin trichloride or dialkyltin dichloride can be varied over a wide range, but in general, a stoichiometric quantity should be employed, varying depending upon whether solvolysis of 1, 2 or 3 tin-chlorine bonds is desired. When all three chlorides are replaced in a monoalkyltin trichloride, monoalkyl stannanoic acid and anhydrides thereof are formed.

Acyloxy groups are obtained for X, Y and -O-R by the addition to the reaction mixture of an alkali metal carboxylic acid salt containing from 1 to 22 carbon atoms. Again, a stoichiometric quantity should be employed, varying depending upon whether the replacement of 1, 2 or 3 chlorine atoms per tin atom is desired.

Upon completion of the reaction followed by washing with dilute aqueous caustic, esters of carboxylic acids prepared in accordance with the present invention will contain less than about 400 ppm of tin, when the active catalyst has a ratio of carbon atoms in A and X (when A and/or X are alkyl groups) for each Sn of two or less. The reaction product will preferably contain less than about 100 ppm tin, and ideally contain less than about 25 ppm of tin. Esters of carboxylic acids prepared in accordance with the present invention, in which the catalyst has a ratio of carbon atoms in A and X (when A and/or X are alkyl groups) for each Sn of four or less, may contain up to about 1200 ppm of tin.

For transesterification reactions utilizing unsaturated carboxylic acid ester starting materials, or unsaturated monohydric or polyhydric alcohol starting materials, it is critical that polymerization of the unsaturated bonds be inhibited with one or more polymerization inhibitors. Such inhibitors are well know to those skilled in the art and include, but are not limited to, hydroquinone and its monomethyl ether, catechol, pyrocatechol, resorcinol, pyrogallol, propyl gallate, and the like.

A common feature of the above-described polymerization inhibitors is that they require the presence of oxygen to function effectively. It is, therefore, necessary to supply a stream of an oxygen containing gas (either air or an air-nitrogen mixture) to the reaction vessel throughout the course of the transesterification reaction when such polymerization inhibitors are employed. The amount of oxygen to be used depends upon the exact product being made as well as on the size of the reactor, and can be readily determined by one of ordinary skill in the art without undue experimentation.

Another feature common to the above-listed polymerization inhibitors is that they all contain one or more phenolic hydroxyl groups. The presence of these phenolic groups enables the inhibitors to form water-soluble sodium salts when contacted with sodium hydroxide solutions. This permits the easy removal of excess phenolic inhibitors from the reaction mixture at the end of the reaction, if desired. Also, as is well understood by those of ordinary skill in the art, if desired, lower levels of inhibitors and/or different inhibitors can be added at this point. In addition, the alkali solubility of the polymerization inhibitors permits the removal from the carboxylic acid ester transesterification reaction product both the polymerization inhibitor and the residual organotin transesterification catalyst by the same washing procedure.

The caustic washing step is performed with from about 10% to 30% by weight of a caustic solution in an amount between about 10% and about 100% of the batch weight. A 15% to 20% by weight caustic solution is preferred. An amount of caustic solution between about 15% and about 25% of the batch weight is preferred, and a caustic solution wash of about 20% of the batch weight is most preferred. Between one to five washes should be performed, with two to three washes being preferred.

Monoalkyl and dialkyltin catalysts can also be removed from transesterification reaction mixtures using a strong aqueous acid wash. An additional wash using caustic is still necessary to remove phenolic inhibitors. This may be advantageous because most monoalkyl and dialkyltin compounds containing about one to four carbon atoms per tin atom will dissolve in both acid and alkali and residual tin in the final product may be further reduced. This is demonstrated in Examples 7 and 8 where butylstannanoic acid anhydride is used as catalyst. Isodecyl methacrylate washed with acid followed by washing with base has lower residual tin (140 ppm Sn) than isodecyl methacrylate washed with dilute caustic alone (1160 ppm Sn).

The aqueous acid wash should have a pH less than about 1.5. Suitable acids include hydrochloric and methanesulphonic, phosphoric, sulfuric, and hydrobromic. Preferred acids are hydrochloric and hydrobromic. The acids are preferably used in concentrated form, although diluted solutions are suitable as well.

The amount of the acid wash should also be between about 10% and about 100% of the batch weight, with an amount between about 15% and about 25% of the batch weight being preferred. An acid wash of about 20% of the batch weight is also most preferred. From one to five acid washes should also be performed, with two or three washes being preferred.

The combination of techniques described above permits the preparation of higher esters of carboxylic acids by transesterification as "bottoms" products on an industrial scale. In addition to high purity and high product yields, the ester is produced essentially free of the organotin reaction catalyst.

The following non-limiting examples set forth hereinbelow illustrate certain aspects of the present invention. They are not to be considered limiting as to the scope and nature of the present invention. In the examples which follow, all parts are parts by weight, and the term "molar ratio" refers to the molar ratio of alkali to dimethyltin dichloride.

EXAMPLES

Unless otherwise noted, reagents were obtained from either Witco (Argus) Corporation of Greenwich, Conn., Atochem of Philadelphia, Pa., Cardinal Chemical of Columbia, S.C., or Gelest of Tullytown, Pa. Residual tin values in the following examples were determined by Atomic Absorption Spectroscopy.

EXAMPLE 1

Preparation of Neopentyl Glycol Diacrylate Using Dimethyltin Dichloride/Tetramethyldiacetoxydistannoxane, (2:1) As Catalyst A mixture of neopentyl glycol (104 parts), methyl acrylate (200 parts), heptane (50 parts), dimethyltin dichloride (3.6 parts), tetramethyldiacetoxydistannoxane (3.6 parts), 4-methoxyphenol (0.3 parts) and hydroquinone (0.3 parts) was heated under reflux using a fractionating column. Methanol, heptane, and excess methyl acrylate were removed from the crude product. To remove the tin catalyst and polymerization inhibitors, the crude product containing approximately 50% solvent was washed twice with 15% sodium hydroxide at 20% of batch weight. After reducing alkalinity by washing the product with a 15% sodium chloride brine solution, the organic layer was concentrated to yield 186 parts (88% yield based on neopentyl glycol) of neopentyl glycol diacrylate. The purity of the final product was 95%. Analysis for residual tin was 300 ppm.

EXAMPLE 2

Preparation of 1,3-Butylene Glycol Dimethacrylate Using Dimethyltin Dichloride/Sodium Acetate (1:1) As Catalyst A mixture of 1,3-butylene glycol (90 parts), dimethyltin dichloride (5.5 parts), sodium acetate (2.0 parts), 4-methoxyphenol (0.3 parts), hydroquinone (0.3 parts), heptane (50 parts) and methyl methacrylate (300 parts) was heated as in Example 1. Methanol, heptane, and excess methyl methacrylate were removed from the crude product. To remove the tin catalyst and polymerization inhibitors, the crude product containing approximately 50% solvent was washed twice with 15% sodium hydroxide at 20% of batch weight. After reducing alkalinity by washing the product with a 15% sodium chloride brine solution, the organic layer was concentrated to yield 203 parts (90% yield based on 1,3-butylene glycol) of 1,3-butylene glycol dimethacrylate (BGDMA). The purity of the final product was greater than 98%. Analysis for residual tin was 320 ppm.

EXAMPLE 3

Preparation Of Ethylene Glycol Dimethacrylate Using Butyltin Trichloride/Sodium Methoxide (1:1) As Catalyst A mixture of ethylene glycol (62.0 parts), methyl methacrylate (300 parts), heptane (50 parts), butyltin trichloride (7.0 parts), sodium methoxide (5.4 parts, 25% in methanol), 4-methoxyphenol (0.5 parts) and hydroquinone (0.5 parts) was heated as in Example 1. Methanol, heptane, and excess methyl methacrylate were removed from the crude product. To remove the tin catalyst and polymerization inhibitors, the crude product containing approximately 50% solvent was washed twice with 15% sodium hydroxide at 20% of batch weight. After reducing alkalinity by washing the product with a 15% sodium chloride brine solution, the organic layer was concentrated to yield 185 parts (93% yield based on ethylene glycol) of ethylene glycol dimethacrylate (EGDMA). The purity of the final product was greater than 98%. Analysis for residual tin was 160 ppm.

EXAMPLE 4

Preparation Of Cyclododecyl Methacrylate Using Monobutyltin Dihydroxide Monochloride As Catalyst Monobutyltin dihydroxide monochloride (6.0 parts) was heated under vacuum to oligomerize it. To the oligomerized catalyst was added cyclododecanol (184 parts), 4-methoxyphenol (0.5 parts), hydroquinone (0.5 parts), heptane (50 parts) and methyl methacrylate (300 parts) and the reaction mixture was heated as in Example 1. Methanol, heptane, and excess methyl methacrylate were removed from the crude product. To remove the tin catalyst and polymerization inhibitors, the crude product containing approximately 50% solvent was washed three times with 159 sodium hydroxide at 20% of batch weight. After reducing alkalinity by washing the product with a 15% sodium chloride brine solution, the organic layer was concentrated to yield 228 parts (90% based on cyclododecanol) yield of cyclododecyl methacrylate. The purity was greater than 98%. Analysis for residual tin was 740 ppm.

EXAMPLE 5

Preparation Of Isobornyl Acrylate Using Methyltin Trichloride/Sodium Methoxide As Catalyst Isoborneol (154 parts), methyl acrylate (200 parts), heptane (50 parts), methyltin trichloride (12 parts), sodium methoxide (25% in methanol, 10.8 parts), 4-methoxyphenol (0.3 parts), and hydroquinone (0.3 parts) were heated as in Example 1. Methanol, heptane, and excess methyl acrylate were removed from the crude product. To remove the tin catalyst and polymerization inhibitors, the crude product containing approximately 50% solvent was washed twice with 20% sodium hydroxide at 20% of batch weight. After reducing alkalinity by washing the product with a 15% sodium chloride brine solution, the organic layer was concentrated to yield 166 parts (80% yield, based on isoborneol). The purity of the final product was greater than 95%. Analysis for residual tin was 25 ppm.

EXAMPLE 6

Preparation Of 1-Dodecyl Acrylate Using Butylstannanoic Acid As Catalyst

A mixture of 1-dodecanol (186 parts), butylstannanoic acid (5.2 parts), 4-methoxyphenol (0.5 parts), hydroquinone (0.5 parts), heptane (28 parts) and methyl acrylate (200 parts) was heated together as in Example 1. Methanol, heptane, and excess methyl acrylate were removed from the crude product. To remove the tin catalyst and polymerization inhibitors, the crude product containing about 50% solvent was washed three times with 20% sodium hydroxide at 20% of batch weight. After reducing alkalinity by washing the product with a 15% sodium chloride brine solution, the organic layer was concentrated to yield 188 parts (79% based on 1-dodecanol) of 1-dodecyl acrylate. The purity of the final product was 98%. Analysis for residual tin was 980 ppm.

EXAMPLE 7

Preparation Of Isodecyl Methacrylate Using Butylstannanoic Acid Anhydride As Catalyst A mixture of isodecanol (158 parts), butylstannanoic acid anhydride (5.0 parts), 4-methoxyphenol (1.0 parts), hydroquinone (1.0 parts), heptane (28 parts), and methyl methacrylate (300 parts) was heated as in Example 1. Methanol, heptane, and excess methyl methacrylate were removed from the crude product. To remove the tin catalyst and polymerization inhibitors, the crude product containing approximately 50% solvent was washed twice with 15% sodium hydroxide at 20% of batch weight. After reducing alkalinity by washing the product with a 15% sodium chloride brine solution, the organic layer was concentrated to yield 185 parts (82% based on isodecanol). The purity of the final product was 96%. Analysis for residual tin was 1160 ppm.

EXAMPLE 8

Preparation Of Isodecyl Methacrylate Using Butylstannanoic Acid Anhydride As Catalyst, An Acid Wash and A Caustic Wash To Remove Tin A mixture of isodecanol (158 parts), butylstannanoic acid anhydride (5.0 parts), 4-methoxyphenol (1.0 parts), hydroquinone (1.0 parts), heptane (28 parts), and methyl methacrylate (300 parts) was heated as in Example 1. Methanol, heptane, and excess methyl methacrylate were removed from the crude product. To remove the tin catalyst and polymerization inhibitors, the crude product containing about 50% solvent was washed twice with concentrated hydrochloric acid (37%) at 20% of batch weight. This was followed by a 20% sodium hydroxide wash at 20% of batch weight. After reducing alkalinity by washing the product with a 15% sodium chloride brine solution, the organic layer was concentrated to yield 199 parts (88% based on isodecanol). The purity was 97%. Analysis for residual tin was 140 ppm.

EXAMPLE 9

Preparation Of Isodecyl Methacrylate Using Butylstannanoic Acid As Catalyst, An Acid Wash and A Caustic Wash To Remove Tin A mixture of isodecanol (158 parts), butylstannanoic acid anhydride (5.0 parts), 4-methoxyphenol (1.0 parts), hydroquinone (1.0 parts), heptane (28 parts), and methyl methacrylate (300 parts) was heated as in Example 1. Methanol, heptane, and excess methyl methacrylate were removed from the crude product. To remove the tin catalyst and polymerization inhibitors, the crude product containing about 50% solvent was washed once with concentrated hydrobromic acid (48%) at 25% of batch weight. This was followed by two 20% sodium hydroxide washes at 25% of batch weight. After reducing alkalinity by washing the product with a 15% sodium chloride brine solution, the organic layer was concentrated to yield 208 parts (92.4% based on isodecanol). The purity was 98%. Analysis for residual tin was 100 ppm.

The level of tin in product ester is generally observed to increase with decreasing solubility of the organotin catalyst in aqueous alkali. Solubility of the organotin catalyst generally decreases as the atomic ratio of carbon to tin in the organotin catalyst increases. The data below taken from the foregoing examples demonstrates that the practical limit of the ratio of carbon atoms in A and X (when A and/or X are alkyl groups) for each tin atom required for significant extractability (i.e. greater than about 90%) is about 4 or less.

| Example No. | Catalyst System | C/Sn Ratio | Sn, ppm | Sn Extracted |
|---|---|---|---|---|
| 1 | Dimethyltin dichloride/ tetramethyldiacetoxy- distannoxane (2:1) | 2 | 300 | 98.4% |
| 2 | Dimethyltin dichloride/ sodium acetate | 2 | 320 | 97.6% |
| 3 | Monobutyltin (trichloride)/ sodium methoxide (1:1) | 4 | 160 | 98.9% |
| 4 | Monobutyltin (dihydroxide monochloride) | 4 | 740 | 93.8% |
| 5 | Monomethyltin trichloride/ sodium methoxide (1:1) | 1 | 25 | 99.8% |
| 6 | Butyl stannanoic acid | 4 | 980 | 92.2% |
| 7 | Butyl stannanoic acid anhydride (Monobutyltin oxide) | 4 | 1160 | 91.2% |
| 8 | Butyl stannanoic acid anhydride (Monobutyltin oxide) | 4 | 140 | 98.9% |
|  | Butyl Stannanoic acid | 4 | 100 | 99.2% |

As will now be readily appreciated, the present invention provides a simplified method for removing organotin catalysts as well as phenolic polymerization inhibitors from carboxylic acid ester reaction products. The present invention, therefore, satisfies a long-felt and heretofore unmet need for organotin catalyst-free transesterification reaction products.

The foregoing description of the preferred embodiment should be taken as illustrative, rather than as limiting, the present invention as defined by the claims. Numerous variations and combinations of the features described above can be utilized without departing from the present invention.

What is claimed is:

1. A method for transesterifying methyl or ethyl esters of carboxylic acids with alcohols and polyols comprising the steps of:

(A) providing a reaction mixture comprising:

(1) an alcohol or polyol selected from the group consisting of aralkyl, aliphatic and cycloaliphatic alcohols and polyols; and (2) a methyl or ethyl ester of a carboxylic acid selected from the group consisting of mono- and polycarboxylic acids;

provided that said reaction mixture does not include a mixture of a polyol with a polycarboxylic acid;

(B) reacting said mixture at a temperature at which said alcohol or polyol and said carboxylic acid are liquid, and in the presence of a catalytically effective amount of an organotin catalyst having the structure:

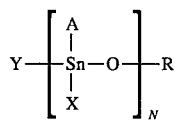

wherein, for each Sn, A is independently selected from the group B consisting of alkyl groups containing from one to four carbon atoms and X is independently selected from the group consisting of alkyl, chlorine, bromine, hydroxyl, 1 to 18 carbon atom alkoxy and 1 to 18 carbon atom acyloxy groups, provided that when X is alkyl, the total number of carbon atoms in A and X for each Sn is no more than 4, and when X is not alkyl, the total number of carbon atoms in A for each Sn is no more than 4;

Y is selected from the group consisting of chlorine, bromine, hydroxyl, 1 to 18 carbon atom alkoxy and 1 to 18 carbon atom acyloxy groups; R is selected from the group consisting of hydrogen, 1 to 18 carbon atom alkyl and 1 to 18 carbon atom acyl groups or Y, X and -O-R together form a stannanoic acid group or an anhydride thereof; and N is an integer from 1 to 10;

so that an alcohol or a polyol ester of said carboxylic acid and methanol or ethanol are formed;

(C) washing said reaction mixture with aqueous alkali having a pH greater than about 13.2 so as to remove essentially all of said organotin catalysts; and (D) recovering said alcohol or polyol carboxylic acid ester essentially free of said organotin catalyst.

2. The method of claim 1, wherein said reacting step comprises heating said reaction mixture.

3. The method of claim 2, wherein said reaction mixture includes a catalytically effective amount of a monoalkyltin trichloride or a dialkyltin dichloride having no more than four carbon atoms in said alkyl groups attached to each tin atom and said heating step comprises heating said monoalkyltin trichloride or said dialkyltin dichloride so that said organotin catalyst is formed in situ.

4. The method of claim 3, wherein said reaction mixture includes an HCl-acceptor compound so as to promote the formation of said organotin catalyst.

5. The method of claim 4, wherein said reaction mixture comprises up to about a 3:1 molar ratio of said HCl-acceptor compound to said monoalkyltin trichloride, or up to about a 2:1 molar ratio of said HCl-acceptor compound to said dialkyltin dichloride.

6. The method of claim 4, wherein said HCl-acceptor compound is selected from the group consisting of alkali metal hydroxides, alkoxides and carboxylates containing from 1 to 18 carbon atoms, carbonates and bicarbonates, alkaline earth metal oxides, hydroxides, carbonates, bicarbonates, carboxylates, and organic bases.

7. The method of claim 6, wherein said alkali metal hydroxides, alkoxides, carbonates, bicarbonates, and carboxylates are selected from the group consisting of lithium, sodium and potassium hydroxides, alkoxides, carbonates and bicarbonates.

8. The method of claim 6, wherein said alkali metal alkoxides are selected from the group consisting of alkali metal methoxides, ethoxides and alkoxides of said alcohols and polyols.

9. The method of claim 2, wherein said reaction mixture includes a catalytically effective amount of a monoalkyltin dihydroxide monochloride having no more than four carbon atoms, and said heating step comprises preheating said monoalkyltin dihydroxide monochloride under vacuum before adding said reactants, so that an oligomeric polystannoxane catalyst is formed.

10. The method of claim 2, wherein said heating step comprises heating said reaction mixture so that said methanol or ethanol is removed from said reaction mixture, thereby permitting the reaction step to run to completion.

11. The method of claim 1, wherein said methyl or ethyl ester comprises a methyl or ethyl ester of an unsaturated mono- or polycarboxylic acid.

12. The method of claim 11, wherein said unsaturated carboxylic acid is selected from the group consisting of acrylic acid and methacrylic acid.

13. The method of claim 1, wherein said reaction mixture comprises a polyol.

14. The method of claim 1, wherein said reaction mixture comprises an alcohol.

15. The method of claim 1, further including the step of washing said reaction mixture with an aqueous acid at a pH less than about 1.5 before said step of washing said reaction mixture with said alkali.

16. The method of claim 15, wherein said aqueous acid is selected from the group consisting of methanesulphonic, sulfuric, phosphoric, hydrochloric, and hydrobromic.

17. The method of claim 16, wherein said aqueous acid is selected from the group consisting of hydrochloric and hydrobromic.

18. The method of claim 1, wherein said organotin catalyst comprises a mixture of organotin compounds selected from the group consisting of alkyl tin trichlorides and dialkyl tin dichlorides.

19. The method of claim 1, wherein said organotin catalyst comprises a mixture of organotin compounds selected from the group consisting of dialkyl tin oxides, dialkyl tin dialkoxides and dialkyl tin dicarboxylates.

* * * * *

UNITED STATES PATENT AND TRADEMARK OFFICE
CERTIFICATE OF CORRECTION

PATENT NO. : 5,606,103
DATED : February 25, 1997
INVENTOR(S) : Trapasso et al.

It is certified that error appears in the above-identified patent and that said Letters Patent is hereby corrected as shown below:

Column 2, line 61, "micelies" should read --micelles--.

Column 9, line 50, "Situ" should read --situ--.

Column 10, line 35, "oxygen containing" should read --oxygen-containing--.

Column 12, line 61, "159" should read --15%--.

Column 14, line 63, within the table, the last line under the first column "Example No.", before "Butyl Stannanoic acid" should read --9--.

Column 15, line 33, "group B consisting" should read --group consisting--.

Signed and Sealed this

Sixth Day of May, 1997

Attest:

BRUCE LEHMAN

Attesting Officer

Commissioner of Patents and Trademarks